US00PP31478P2

(12) United States Plant Patent
Hansen

(10) Patent No.: US PP31,478 P2
(45) Date of Patent: Feb. 25, 2020

(54) ***HIBISCUS* PLANT NAMED 'HOLY GRAIL'**

(50) Latin Name: ***Hibiscus* hybrid (L.)**
Varietal Denomination: Holy Grail

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,349

(22) Filed: Nov. 5, 2018

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608
See application file for complete search history.

*Primary Examiner* — Anne Marie Grunberg

(57) ABSTRACT

A new and distinct cultivar of winter-hardy, herbaceous, perennial, hybrid *Hibiscus* plant named 'Holy Grail' comprising a rounded mound habit of multiple, well-branched, basal stems producing flowers from the bottom to the top of the plant from late July to early September. Flowers have petals with strong red with dark red shiny eye set off with column of light yellow pollen. The foliage is ovate to rarely three-lobed, and deep mahogany-colored and the light green calyces provide sharp contrast.

2 Drawing Sheets

Botanical classification: *Hibiscus* hybrid (L.).
Variety denomination: 'Holy Grail'.

STATEMENT REGARDING PRIOR DISCLOSURES UNDER 37 CFR 1.77(b)(6)

The first publically released photograph of the new plant was on Nov. 28, 2017 when it was pictured on the commercial calendar for Walters Gardens, Inc. The first disclosure, in the form of a sale, was made by Walters Gardens, Inc. on Apr. 2, 2017. Walters Gardens, Inc. obtained the new plant and all information relating thereto, from the inventor. No plants of *Hibiscus* 'Holy Grail' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *hibiscus* plant, *Hibiscus* 'Holy Grail' hybridized under direction of the inventor Aug. 7, 2015 at a wholesale perennial nursery in Zeeland, Mich. The new plant is a hybrid of the complex, unreleased, proprietary hybrid known as 12-166-5 times 'Perfect Storm' U.S. Plant Pat. No. 27,880. Into the trial process the new plant was assigned the breeder code labeled 15-85-1. Both parents have a complex mixture of species in them, comprising the species: *moscheutos* and *coccineus*.

*Hibiscus* 'Holy Grail' was first asexually propagated in late summer of 2016 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Holy Grail' differs from its parents as well as all other hardy herbaceous *hibiscus* known to the applicant in many traits. The most similar *hibiscus* known to the applicant are 'Vintage Wine' U.S. Plant Pat. No. 27,839, 'Robert Fleming' U.S. Plant Pat. No. 14,776, 'Cranberry Crush' U.S. Plant Pat. No. 21,984 and 'Mars Madness' U.S. Plant Pat. No. 27,838 and 'Mars Madness' U.S. Plant Pat. No. 27,838. 'Cranberry Crush' has flower petals are that are more cupped and over lapping, the petal color has a more reddish-orange hue and less reddish-purple, the plant habit is slightly taller and the foliage are deep green rather than the dark mahogany of the new plant. 'Mars Madness' has a lighter magenta-red flower with more overlapping petals and the foliage has less intense mahogany coloration. 'Vintage Wine' has a slightly deeper reddish-purple flower with more overlapping petals, the foliage is more deep green without the strong dark mahogany coloration, and the habit is more upright with less branches and the spreading mound habit of the new plant. 'Robert Fleming' is taller in habit, with similar flowers, but the foliage is deep green and not the deep mahogany of the new plant.

Comparison of the female parent was taller and more upright in habit, the foliage color was not as dark mahogany and it had a different shade of red in flower color. Further comparison with the female parent is not possible as it was not maintained. The male parent, 'Perfect Storm' has similar habit, but the flowers are very light pink to near white with a lustrous bright-red eye zone and veins of bright-red and marginal red tinting on the distal portion, and the foliage is similarly colored deep mahogany but deeply-dissected with three to five lobes.

*Hibiscus* 'Holy Grail' is a unique hardy herbaceous *hibiscus* with the following combined traits:

1. Winter-hardy compact perennial with upright habit of multiple, well-branched, basal stems.

2. Many rotate flowers of strong red produced from bottom to top of plant.
3. Flowers produced over a long period from late July to early September.
4. Flower petals having darker red eye zone set off with column of light yellow pollen.
5. Primarily ovate foliage strongly colored with deep mahogany.
6. The calyces are light green inside and outside, deeply contrasting with the dark foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
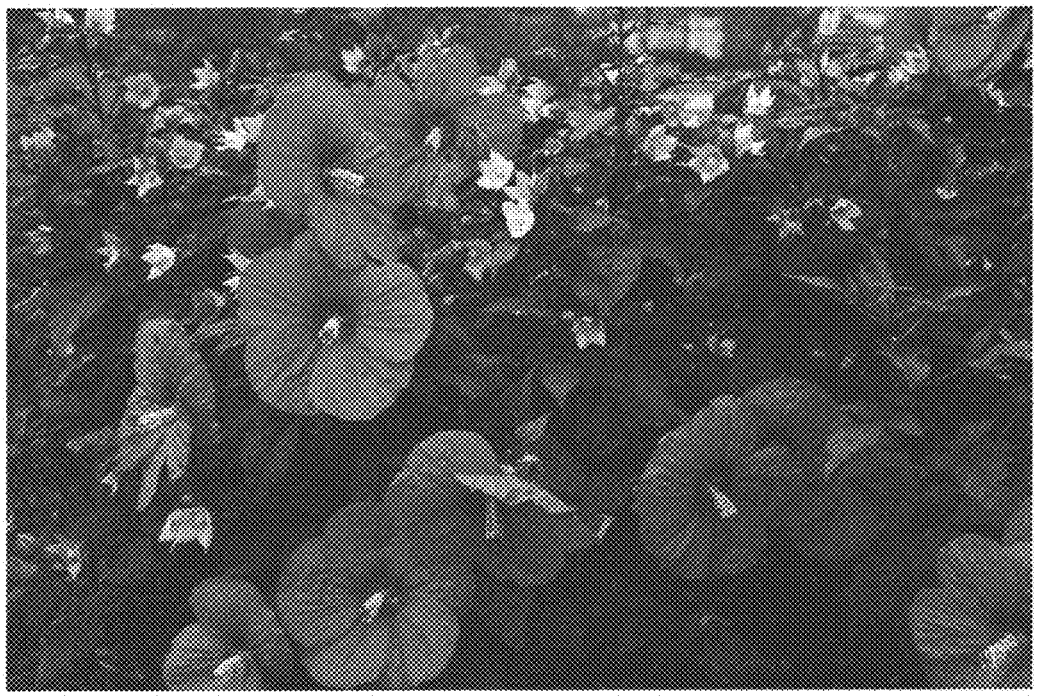
FIG. 1 shows a three-year-old plant in full flower in a trial garden.
Figure 2:
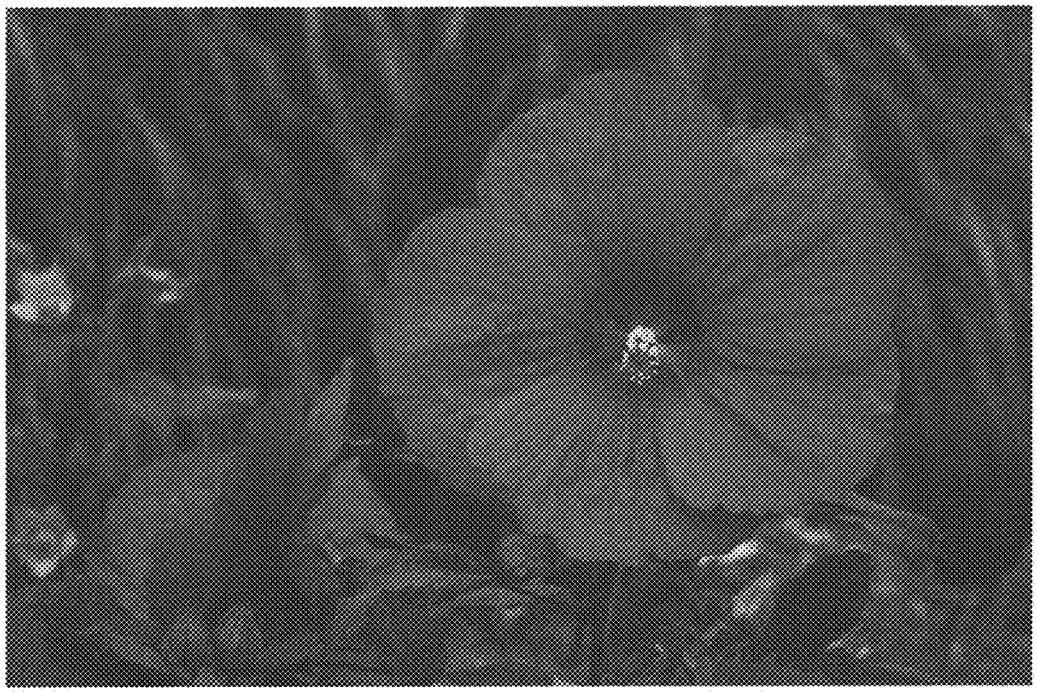
FIG. 2 shows a close-up of the flower and bud.
Figure 3:
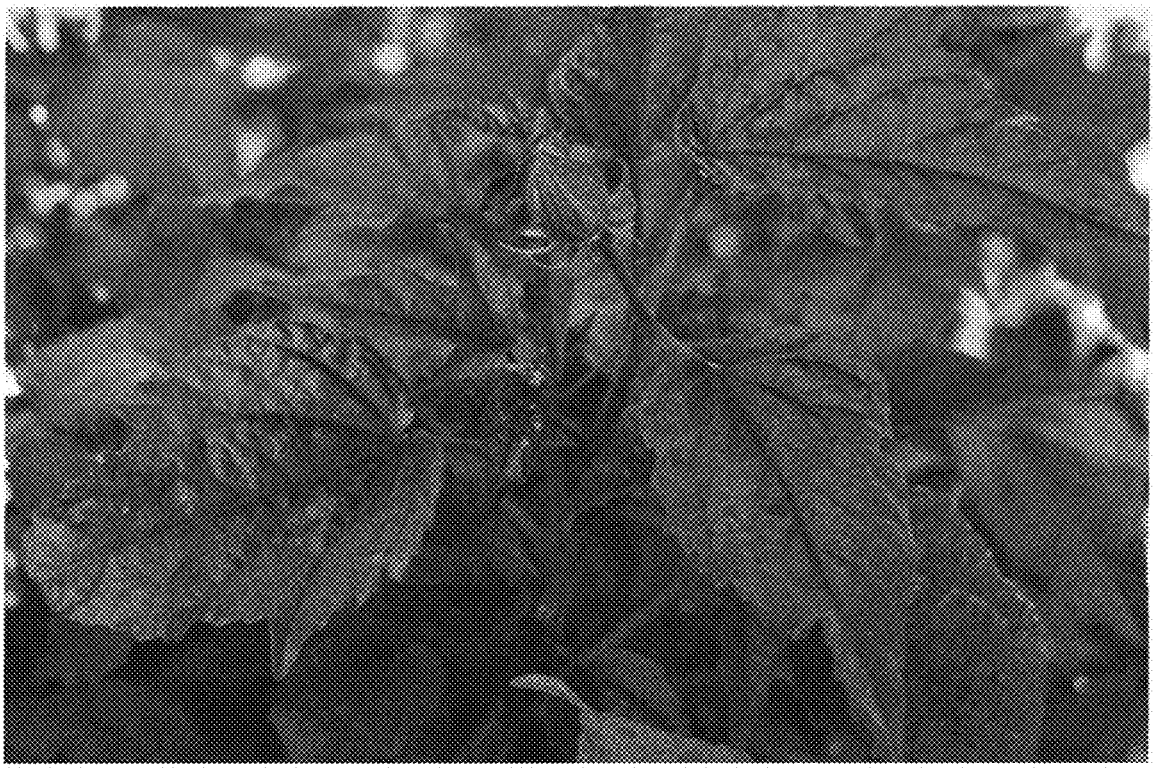
FIG. 3 shows the expanding and mature foliage with stem and young flower bud.

The following descriptions and color references are based on the 2001 edition of The Royal Horticultural Society Colour Chart except where common dictionary terms are used. The new plant, *Hibiscus* 'Holy Grail', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, non-patented, proprietary *hibiscus* known by the breeder code 12-166-5, the male or pollen parent is 'Perfect Storm';

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.8 cm diameter, fleshy; root color creamy yellow nearest RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 21 thick, upright, heavily-branched stems producing an upright spreading mound to about 80.0 cm tall and about 110.0 cm wide; flowering from base to top of plant with up to about 52 flowers per main stem, average flowers per stem about 36.

*Stem*.—Cylindrical, glabrous, glaucous; to about 80.0 cm tall and about 2.5 cm diameter at base, average about 74.0 cm tall and about 1.4 cm diameter at base.

*Stem color*.—Between RHS 177A and RHS 178A.

*Lateral branches*.—To 11 per stem, average about 8 per stem; cylindrical, glabrous, glaucous; to about 36.0 cm long and 8.0 mm diameter at base, smaller distally.

*Lateral branch color*.—Between RHS 177A and RHS 178A.

*Internode*.—About 7 nodes per stem below branches; average internode length about 2.3 cm of unpinched plant.

*Internode color*.—Same as surrounding stem.

Foliage description: Ovate to tri-lobed; alternate; coarsely and irregularly dentate; apex and side lobes acute; base rounded to nearly cordate; glabrous abaxial and adaxial; shallowly to moderately incised when tri-lobed; adaxial surface lustrous when expanding, slightly lustrous when mature, abaxial surface matte; leaf blades to about 14.5 cm long and about 8.3 cm across, average blade size 11.0 cm long and 7.5 cm wide; no fragrance detected; Foliage color: young expanding leaves — adaxial nearest RHS N186C, abaxial nearest blend between RHS 147B and RHS N138C with irregular highlights around margin nearest RHS 187B; mature leaves - adaxial nearest RHS N186B in high light exposure and nearest RHS NN137B with undertones of nearest RHS N186B, abaxial nearest RHS 147B;

*Veins*.—Palmate; lustrous; costate on abaxial.

*Vein color*.—Young adaxial nearest RHS N186B with midrib nearest RHS N186C, abaxial nearest RHS 185C; mature adaxial nearest RHS 187A and abaxial veins nearest RHS 185D proximally and nearest RHS 185B distally.

*Petioles*.—Mostly cylindrical, proximally slightly applanate on adaxial side near base; glaucous; glabrous; to about 8.0 cm long and 3.0 mm diameter at base, average size about 6.0 cm long and 2.5 mm wide at base.

*Petiole color*.—Nearest RHS 187B.

Flower description: Complete; actinomophic; mostly outward facing; rotate; lasting up to two days on plant; no fragrance detected; to about 21.0 cm across and 6.5 cm deep, decreasing distally;

*Buds one day prior to anthesis*.—Ellipsoidal with rounded apex and bluntly rounded base; sepals adpressed to petals; about 7.6 cm long and about 4.8 cm diameter in middle.

*Bud seven days prior to anthesis, with petals still enveloped in calyx*.—Cylindrical with pointed apex and rounded base; carinate at sepals fusion lines; glabrous, glaucous; about 2.2 cm long and about 1.8 cm across.

*Bud color one day prior to anthesis*.—Exposed petal color between RHS 187C and RHS 60A with lighter veins the same color.

*Bud seven days prior to anthesis*.—Variable, with distal regions generally nearest RHS N186D and proximal regions nearest RHS 146D.

*Epicalyx*.—Typically 9 to 11 per flower; linear; entire, glabrous, with margin micro ciliate; dull surface abaxial and adaxial; sharply acute apex and truncate base, arcuate upwards near apex; about 1.6 cm long and about 1.5 mm wide at base.

*Epicalyx color*.—Adaxial nearest RHS 146A, abaxial nearest RHS 146A with strong tinting of nearest RHS 187A.

*Sepals*.—Five, fused in basal 1.8 cm to form star-shaped hypanthium about 6.0 cm across and 3.3 cm deep; acute apex; glabrous; margin entire, edentate; abaxial and adaxial surfaces matte; about 3.5 cm long, about 1.8 cm wide at fusion.

*Sepal color*.—Adaxial base nearest RHS 146D and distal lighter than RHS 146D, veins lighter than RHS 145B; abaxial nearest RHS 138B, with veins and distal tinting nearest RHS 187B.

*Flowers*.—Solitary, up to 52 per main stem without pinching; nearly flat face; mostly outwardly facing; natural spread to about 22.0 cm across and 6.0 cm deep from stigma to base of calyx; smaller in later season.

*Flower lastingness*.—Persist for one to two days; effective for at least 7 weeks beginning late July.

*Flower fragrance*.—No detectable fragrance.

*Petals*.—Five; microscopically puberulent abaxial and adaxial, glabrous eye; adnate to the androecium to form a column, imbricate to about 60% overlapping at widest part (petals overlapping 60% to the petals on either side); palmately veined, primary veins impressed on adaxial and slightly costate abaxial; surface slightly dimpled; rounded with distinct claw and limb; margins: entire, edentate; apex rounded; base short claw-like; Petal size: average about 11.0 cm across and about 11.7 cm long, claw base about 7.5 mm across (smaller in later part of flowering season).

*Petal color*.—Adaxial nearest RHS 46A with darker eye nearest RHS 183B; abaxial basal nearest RHS 46A.

*Flower lastingness*.—One to two days.

*Gynoecium*.—Single; partially enclosed in column. Column: glabrous and lustrous, except base micro-puberulent; about 4.8 cm long and about 8.0 mm across at base; with pistil exserted about 8.0 mm. Column color: mixture between RHS 61B and RHS 61A. Style: micro-puberulent in region exserted above column; about 4.6 cm long, penta-furcate in about distal 6.0 mm; branch diameter about 1.2 mm; color nearest RHS 187C. Stigma: typically five; flattened globose, puberulent, about 2.5 mm in diameter and 2.0 mm tall; color between RHS 187B and RHS 187C. Ovary: superior, semi-globose, rounded to broadly acute apex and flat truncate base; about 9.0 mm across at base and about 6.0 mm tall; acute apex; color between RHS 145C and RHS 145D.

*Androecium*.—Filaments: numerous, about 100; about 4.0 mm long and about 0.2 mm diameter; attached along nearly the entire length of column; color nearest RHS 61B proximally and center, nearest RHS NN155D distally. Anthers: flattened ellipsoid; dorsifixed; about 2.5 mm long and 2.0 mm across and about 0.8 mm thick; color nearest RHS 10B. Pollen: abundant, globose, less than 0.1 mm long; color nearest RHS 10B.

Pedicel: Cylindrical, glabrous, glaucous; length from base of sepal to abscission point about 2.0 cm long, from abscission point to stem node about 6.5 cm long; about 3.0 mm wide; longer on early flowers and decreasing in distal flowers; color nearest between RHS 177A and RHS 178A;

Peduncle: Cylindrical, glabrous, glaucous; flowering in the distal 39.0 cm; color between RHS 177A and RHS 178A;

Fruit: Penta-loculicidal capsule; pubescent along inner septa, glabrous outside; ellipsoidal, cuspidate apex and flattened base; about 25.0 mm long and 20.0 mm diameter; color nearest RHS 200A when mature; up to 72 seeds per fruit;

Seed: Minutely floccose; globose; about 2.4 mm in diameter; color nearest RHS N200A;

Resistance: *Hibiscus* 'Holy Grail' has not displayed any pest and disease resistance beyond that typical of hardy perennial *hibiscus*. The plant grows best with plenty of moisture. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Holy Grail' as herein illustrated and described.

* * * * *